United States Patent
Ma et al.

(10) Patent No.: US 10,308,951 B2
(45) Date of Patent: Jun. 4, 2019

(54) **APPLICATION OF *IPS1* GENE IN IMPROVING PHOTOSYNTHESIS OF RICE**

(71) Applicant: Zhejiang Normal University, Jinhua, Zhejiang (CN)

(72) Inventors: Bojun Ma, Zhejiang (CN); Xifeng Chen, Zhejiang (CN)

(73) Assignee: Zhejiang Normal University, Jinhua (CN)

( * ) Notice: Subject to any disclaimer, the term of this patent is extended or adjusted under 35 U.S.C. 154(b) by 29 days.

(21) Appl. No.: 15/805,104

(22) Filed: Nov. 6, 2017

(65) Prior Publication Data
US 2019/0136253 A1    May 9, 2019

(51) Int. Cl.
*C12N 15/82* (2006.01)

(52) U.S. Cl.
CPC .................. *C12N 15/8269* (2013.01)

(58) Field of Classification Search
None
See application file for complete search history.

(56) References Cited

FOREIGN PATENT DOCUMENTS

WO    WO 03/008540 A2 *  1/2003

* cited by examiner

*Primary Examiner* — Cathy Kingdon Worley

(57) ABSTRACT

A method for improving photosynthesis of rice includes the step of knocking out IPS1 gene in rice. The IPS1 gene has a nucleotide sequence shown in SEQ ID NO: 1.

1 Claim, 2 Drawing Sheets
Specification includes a Sequence Listing.

APPLICATION OF IPS1 GENE IN IMPROVING PHOTOSYNTHESIS OF RICE

REFERENCE TO SEQUENCE LISTING

The substitute Sequence Listing is submitted to replace the previously submitted Sequence Listing as an ASCII formatted text filed via EFS-Web, with a file name of "Substitute_Sequence_Listing.TXT", a creation date of Nov. 15, 2017, and a size of 2,261 bytes. The substitute Sequence Listing filed via EFS-Web is part of the specification and is incorporated in its entirety by reference herein.

TECHNICAL FIELD

The present invention relates to a gene which can improving photosynthesis of rice and the application thereof, belonging to the field of crops molecular genetics.

BACKGROUND ART

Rice is one of the most important crops in the world. Photosynthesis, which uses energy from sunlight to produce glucose from carbon dioxide and water, is a key factor in biomass synthesis during rice growth. Identification of genes with the function of high photosynthetic efficiency has an important application prospect.

CRISPR (clustered regularly interspaced short palindromic repeats)/Cas9 technology is a significant improvement of genome editing tools for gene functional analysis. A single guide RNA (sgRNA) is generated to direct Cas9 nuclease to a specific genomic location, and Cas9-induced double strand breaks are repaired. The repair is error prone and thus insertions/deletions may be introduced that can disrupt gene function by frame-shift mutation. Therefore, CRISPR/Cas9 can efficiently be used for knockout of target gene, and has been widely used in researches of gene function and application of molecular breeding.

SUMMARY

The technical problem of the invention is to provide an application in which a gene can effectively improve photosynthesis of rice.

In order to solve this problems, the present invention provides an application of a rice gene IPS1 in improving rice photosynthesis; that is knockout of IPS1 gene can effectively improve photosynthesis of rice.

The technical scheme of the invention is as follows:

By using the CRISPR/Cas9 technique, a sgRNA specific targeting IPS1 gene (SEQ ID NO: 1) was designed to knock out the IPS1 gene in wildtype rice Nipponbare, and two IPS1 knockout mutants ips1-1 and ips1-2 were obtained.

PCR amplification and sequencing showed that the mutations occurred at different positions of IPS1 gene (FIG. 1A and FIG. 1B), but all resulted in frame-shift mutations leading to lose function of IPS1 gene.

The sequences of the two knockout mutants above were ips1-1 (SEQ ID NO: 2) and ips1-2 (SEQ ID NO: 3), respectively.

The tow IPS1 gene mutants and the wildtype control Nipponbare were planted in rice field, and the important parameters of photosynthesis in rice flag leaves were assayed in heading stage. Comparing to the wildtype control Nipponbare, the Net photosynthesis rate, stomatal conductance and transpiration significantly increased both in the two mutants (Form 1). These results suggest that knockout of IPS1 gene can effectively improve photosynthesis in rice, and has an important value in high yield breeding.

FORM 1

| Photosynthetic parameters | Nipponbare | ips1-1 | Spi1-2 |
|---|---|---|---|
| Net phosynthetic rate ($\mu mol\ CO_2\ m^{-2}s^{-1}$) | 15.8 ± 0.48 | 19.5 ± 0.60** | 19.1 ± 0.58** |
| Intercellular $CO_2$ concentration ($\mu mol\ CO_2\ mol^{-1}$) | 302 ± 37 | 335 ± 26 | 298 ± 34 |
| Stomatal conductance ($mol\ H_2O\ m^{-2}S^{-1}$) | 0.22 ± 0.04 | 0.41 ± 0.07** | 0.30 ± 0.05* |
| Transpiration ($mmol\ H_2O\ m^{-2}S^{-1}$) | 5.9 ± 0.85 | 8.4 ± 0.57** | 8.9 ± 1.35** |

Form 1 shows the photosynthetic parameters of two IPS1 gene mutants and the wildtype control Nipponbare. '*' and '**' indicate the significant (P<0.05) and the extremely significant (P<0.01) by t-test, respectively, between IPS1 gene mutants and the wildtype control Nipponbare.

BRIEF DESCRIPTION OF THE DRAWINGS

The specific embodiments of the present invention are described in detail with the accompanying drawings.

DETAILED DESCRIPTION

1. Construction of IPS1-Gene CRISPR/Cas9 Vector

Figure 1A:
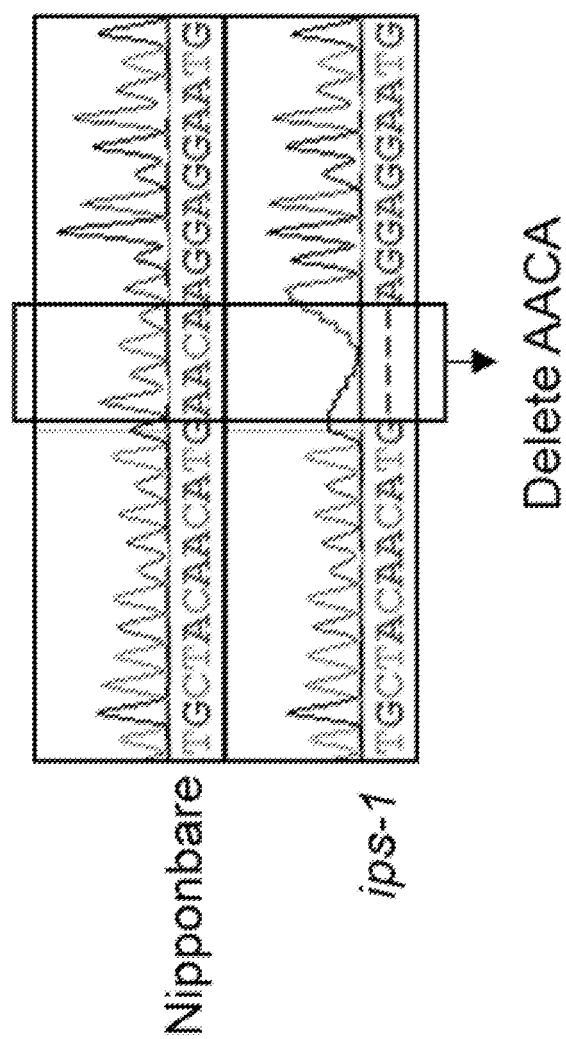
FIG. 1A and FIG. 1B show the sequences analysis of mutation sites in rice IPS1 gene. Nipponbare: the wildtype control (SEQ ID NO: 1); ips1-1 (SEQ ID NO: 2) and ips1-2 (SEQ ID NO: 3): two different knockout mutants of IPS1 gene.
Figure 1B:
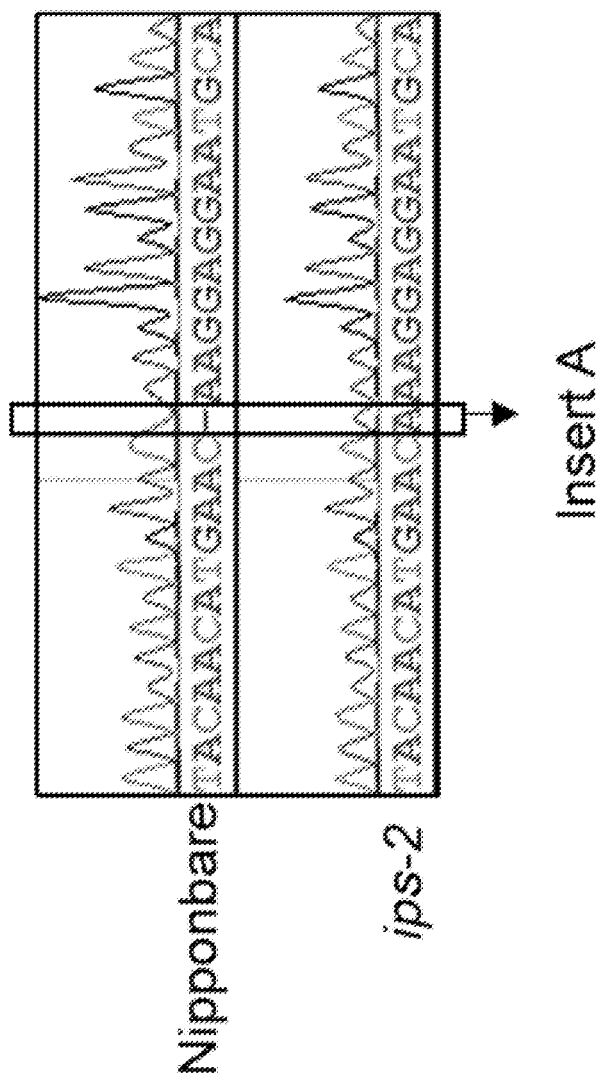

Based on the IPS1 gene sequence (SEQ ID NO: 1), a IPS1-targeting sgRNA sequence, 5'-CTGCTACAACAT-GAACAAGGAGG-3' (SEQ ID NO: 4), was designed by program CRISPR Design (crispr.mit.edu/) and synthesized by biotechnology company (e.g. Invitrogen). Then, a CRISPR/Cas9 vector was constructed with this sgRNA using the CRISPR/Cas9 Kit (Biogle, Cat# BGK03) by the product manual.

2. Rice Genetic Transformation of CRISPR/Cas9 Vector

Agrobacterium-mediated transformation of rice were followed by the method described by Nishimura's (Nishimura et al, Nat Protoc, 2006). The CRISPR/Cas9 vector was transformed into wildtype rice variety Nipponbare.

3. Sequence Analysis of sgRNA-Targeted Loci in Transgenic Rice

Total genomic DNA was extracted from rice leaves using SDS method: grind 0.1 g flesh leaves with Liquid nitrogen into powder; transfer the tissue powder into a microcentrifuge tube, and add 600 μl lysis solution (0.1 mol/L Tris-Cl pH8.0, 500 mmol/L NaCl, 1.25 g/L SDS), and incubate the tube at 65° C. for 60 min. Add 200 μl 5M KAC and vortex, and incubate on ice for 10 min; Add 500 μl chloroform and vortex, and then centrifuge at 10000 r/m for 5 min. Transfer 500 μL of supernatant to a fresh microcentrifuge tube containing 500 μL isopropanol and overturn gently, and centrifuge at 12000 r/m for 3 min. Discard supernatant and add 500 μL 75% ethanol, and centrifuge at 12000 r/m for 3 min. Discard supernatant and dry DNA for 15 min. Add 30 μL ultrapure $H_2O$ to dissolve the DNA.

GoTaq® Master Mix (Promega, USA) was used for PCR amplification of IPS1 gene according to the manufacturer's instructions. The specific PCR primers of IPS1 gene were:

5'-GAGCTGCAAGGCTCTCTCGC-3'    (SEQ ID NO: 5)
and
5'-CATGCATGCACCTAGTCGTCGT-3',    (SEQ ID NO: 6)

synthesized by biotechnology company (e.g. Invitrogen). The PCR process was performed as: (1) 94° C. for 5 min; (2) 94° C. for 30 s, 55° C. for 30 s and 72° C. 60 s, 35 cycles; (3) 72° C. for 5 min. The PCR products were examined via 1% agarose-gel electrophoresis and stained with ethidium bromide. Then the PCR products were send to the biotechnology company (e.g. Invitrogen) for sequencing, and the resulting sequences from the transgenic rice and the wildtype control Nipponbare were compared by program Seq-Man, and two homologous mutants of IPS1 gene were identified and named as ips1-1 and ips1-2. For the ips1-1 mutant, nucleotides 'AACA' were deleted in IPS1 gene; for ips1-2 mutant, an additional nucleotide 'A' was inserted into IPS1 gene. Both of them resulted in frame-shift mutation and loss function of IPS1 gene in the mutants.

For IPS1 gene, the nucleotides sequence in mutant ips1-1 is SEQ ID NO: 2, and that in mutant ips1-2 is SEQ ID NO: 3.

4. Photosynthesis Analysis of Transgenic Rice

The IPS1 gene mutants and the wildtype control Nipponbare were planted in rice field by 30 cm×15 cm spacing. At rice heading stage, 10 plants of each lines were randomly selected to analyze Net photosynthesis rate, intercellular $CO_2$ concentration, stomatal conductance and transpiration in rice flag leaves by the instrument Li-6400 (Li-COR, USA) according to the manufacturer's manual. The significant differences of the results between the IPS1 gene mutants and the wildtype control were assayed by the t-test method.

The results indicated that the Net photosynthesis rate, stomatal conductance and transpiration of the IPS1 gene mutants (ips1-1 and ips1-2) were higher than that of the wildtype control Nipponbare, suggesting that knockout of IPS1 gene can effectively improve photosynthesis in rice.

Finally, it is important to note that the above lists are only specific embodiments of the present invention. Obviously, the invention is not limited to the above embodiments, but can also have a lot of deformation. All the deformation that the general technical personnel in this field can directly derive or associate with the contents disclosed in this field should be considered as the scope of protection of the invention.

What is claimed is:

1. A method for increasing photosynthesis of rice, said method comprising the step of knocking out the IPS1 gene in rice, wherein the IPS1 gene has the nucleotide sequence shown in SEQ ID NO: 1 and wherein the increase in photosynthesis is relative to a rice plant having a wild-type IPS1 gene.

* * * * *

SEQUENCE LISTING

```
<160> NUMBER OF SEQ ID NOS: 6

<210> SEQ ID NO 1
<211> LENGTH: 309
<212> TYPE: DNA
<213> ORGANISM: Oryza sativa

<400> SEQUENCE: 1
atggacgacg gcggcggcgg cggcggcggc gactcgtcgc cggcttcgta catcagattg      60
gtgcagcatc tgatcgagaa gtgcatctgc tacaacatga acaaggagga atgcatggag     120
acgctggaga agcacgccaa catcaagccc gtcatcacct ccaccgtgtg gaaggagctt     180
gagaaggaga acagcgagtt cttcgccacg tacaagaagg gccaaggaga ggaaccagcg     240
gagagcaaga gcagtagttc ttcacaggaa gctgctggtt ccaagagatc aggcggagac     300
gacgactag                                                             309

<210> SEQ ID NO 2
<211> LENGTH: 305
<212> TYPE: DNA
<213> ORGANISM: Oryza sativa

<400> SEQUENCE: 2
atggacgacg gcggcggcgg cggcggcggc gactcgtcgc cggcttcgta catcagattg      60
gtgcagcatc tgatcgagaa gtgcatctgc tacaacatga ggaggaatgc atggagacgc     120
tggagaagca cgccaacatc aagcccgtca tcacctccac cgtgtggaag gagcttgaga     180
aggagaacag cgagttcttc gccacgtaca agaagggcca aggagaggaa ccagcggaga     240
gcaagagcag tagttcttca caggaagctg ctggttccaa gagatcaggc ggagacgacg     300
actag                                                                 305

<210> SEQ ID NO 3
<211> LENGTH: 310
<212> TYPE: DNA
<213> ORGANISM: Oryza sativa
```

<400> SEQUENCE: 3

```
atggacgacg gcggcggcgg cggcggcggc gactcgtcgc cggcttcgta catcagattg    60
gtgcagcatc tgatcgagaa gtgcatctgc tacaacatga acaaggagg aatgcatgga   120 gacgctggag aagcacgcca acatcaagcc cgtcatcacc tccaccgtgt ggaaggagct   180
tgagaaggag aacagcgagt tcttcgccac gtacaagaag ggccaaggag aggaaccagc   240
ggagagcaag agcagtagtt cttcacagga agctgctggt tccaagagat caggcggaga   300
cgacgactag                                                         310
```

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4

```
ctgctacaac atgaacaagg agg                                           23
```

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5

```
gagctgcaag gctctctcgc                                               20
```

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6

```
catgcatgca cctagtcgtc gt                                            22
```